(12) United States Patent
White et al.

(10) Patent No.: US 6,867,156 B1
(45) Date of Patent: Mar. 15, 2005

(54) MATERIALS HAVING Z-DIRECTION FIBERS AND FOLDS AND METHOD FOR PRODUCING SAME

(75) Inventors: Edward Jason White, Mauldin, SC (US); Kurtis Lee Brown, Alpharetta, GA (US); John Herbert Conrad, Alpharetta, GA (US); Robert James Gerndt, Roswell, GA (US); Jose Enrique Maldonado, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/538,744

(22) Filed: Mar. 30, 2000

Related U.S. Application Data

(60) Provisional application No. 60/132,028, filed on Apr. 30, 1999.

(51) Int. Cl.[7] .............................. B32B 5/02; B32B 5/08; B32B 3/02; B32B 3/26
(52) U.S. Cl. ....................... 442/334; 442/409; 428/119; 428/92
(58) Field of Search .................................. 442/334, 409, 442/364; 428/119, 86, 92, 93, 120, 221, 292.1; 604/378, 384

(56) References Cited

U.S. PATENT DOCUMENTS

| 255,381 | A | 3/1882 | Doubleday | 19/145 |
|---|---|---|---|---|
| 2,336,743 | A | 12/1943 | Manning | 156/74 |
| 2,336,744 | A | 12/1943 | Manning | 28/119 |
| 2,336,745 | A | 12/1943 | Manning | 264/10 |
| 2,510,229 | A | 6/1950 | Joa | 156/324 |
| 2,886,877 | A | 5/1959 | Frickert et al. | 65/438 |
| 2,931,091 | A | 4/1960 | Breen | 428/370 |
| 2,975,470 | A | 3/1961 | Snelson et al. | 425/151 |

(List continued on next page.)

FOREIGN PATENT DOCUMENTS

| CZ | 235 494 | 11/1986 | |
|---|---|---|---|
| CZ | 263 075 | 1/1990 | |
| DE | 199 37 066 | 2/2000 | |
| EP | 137 644 | 4/1985 | |
| EP | 137644 | * 4/1985 | |
| EP | 295 038 | 12/1988 | |
| EP | 516964 A1 | * 12/1992 | ............ D04H/1/74 |
| EP | 350 627 | 9/1994 | |
| EP | 516 964 | 11/1996 | |
| EP | 673 314 | 9/1998 | |
| EP | 696 333 | 3/1999 | |
| WO | WO 9961693 A1 | * 12/1999 | ........... D04H/11/04 |

OTHER PUBLICATIONS

Radko Krema et al.: *What's New In Highloft Production?*, Nonwovens Industry, 74–78, Oct. 1997.

Primary Examiner—Cheryl A. Juska
(74) Attorney, Agent, or Firm—Pauley Petersen & Erickson

(57) ABSTRACT

A method for producing a material having z-direction waves in which a layer of continuous fibers is conveyed on a first moving surface into a nip formed by the first moving surface and a second moving surface which is traveling at a slower speed than the first moving surface, resulting in formation of a plurality of z-direction loops in the fibers giving loft to the material and a wave pattern producing ridges on both major surfaces of the resultant nonwoven web. The method permits easy real time alignment of manufacturing parameters to produce a variety of materials. The method further produces lofty nonwovens at a commercially viable rate.

22 Claims, 9 Drawing Sheets

Rush Transfer (on-line) 3.0 osy

U.S. PATENT DOCUMENTS

| Patent No. | | Date | Inventor | Class |
|---|---|---|---|---|
| 3,081,207 A | | 3/1963 | Fox | 442/320 |
| 3,086,253 A | | 4/1963 | Joa | 264/121 |
| 3,202,743 A | | 8/1965 | Elmendorf | 264/109 |
| 3,368,934 A | | 2/1968 | Vosburgh, Sr. | 428/195 |
| 3,481,005 A | | 12/1969 | Owens et al. | 19/306 |
| 3,589,956 A | | 6/1971 | Kranz et al. | 264/115 |
| 3,769,115 A | | 10/1973 | Rasmussen et al. | 156/62.2 |
| 3,802,817 A | | 4/1974 | Matsuki et al. | 425/66 |
| 3,849,241 A | | 11/1974 | Butin et al. | 428/137 |
| 3,972,092 A | | 8/1976 | Wood | 425/82.1 |
| 3,972,763 A | | 8/1976 | Wolvin et al. | 156/210 |
| 4,071,925 A | | 2/1978 | Folk | 19/296 |
| 4,089,720 A | | 5/1978 | Haley | 156/181 |
| 4,100,324 A | | 7/1978 | Anderson et al. | 442/344 |
| 4,102,963 A | | 7/1978 | Wood | 264/518 |
| 4,111,733 A | | 9/1978 | Periers | 156/204 |
| 4,340,563 A | | 7/1982 | Appel et al. | 264/518 |
| 4,357,379 A | | 11/1982 | Sloan et al. | 428/113 |
| 4,434,205 A | | 2/1984 | Fujii et al. | 428/218 |
| 4,440,597 A | | 4/1984 | Wells et al. | 162/111 |
| 4,488,928 A | | 12/1984 | Ali Khan et al. | 156/495 |
| 4,548,856 A | | 10/1985 | Ali Khan et al. | 428/171 |
| 4,578,070 A | * | 3/1986 | Holtman | 604/378 |
| 4,582,666 A | | 4/1986 | Kenworthy et al. | 264/557 |
| 4,590,114 A | | 5/1986 | Holtman | 428/171 |
| 4,624,819 A | | 11/1986 | Hartog et al. | 264/510 |
| 4,741,941 A | | 5/1988 | Englebert et al. | 428/71 |
| 4,818,464 A | | 4/1989 | Lau | 264/510 |
| 4,837,067 A | | 6/1989 | Carey, Jr. et al. | 428/108 |
| 4,908,175 A | | 3/1990 | Angstadt | 264/113 |
| 4,955,999 A | | 9/1990 | Schaefer et al. | 65/499 |
| 5,021,050 A | | 6/1991 | Iskra | 604/379 |
| 5,071,615 A | | 12/1991 | Ranzen | 264/510 |
| 5,093,069 A | | 3/1992 | Mellem et al. | 264/510 |
| 5,108,827 A | | 4/1992 | Gessner | 428/219 |
| 5,167,740 A | | 12/1992 | Michaelis et al. | 156/73.1 |
| 5,198,057 A | | 3/1993 | Newkirk et al. | 156/83 |
| 5,227,107 A | | 7/1993 | Dickenson et al. | 264/113 |
| 5,366,793 A | | 11/1994 | Fitts, Jr. et al. | 428/198 |
| 5,382,400 A | | 1/1995 | Pike et al. | 264/168 |
| 5,558,924 A | | 9/1996 | Chien et al. | 428/181 |
| 5,620,545 A | | 4/1997 | Braun et al. | 156/205 |
| 5,658,640 A | | 8/1997 | Berrigan et al. | 428/152 |
| 5,707,468 A | | 1/1998 | Arnold et al. | 156/62.6 |
| 5,725,734 A | | 3/1998 | Herman et al. | 162/111 |
| 5,792,404 A | | 8/1998 | Cree et al. | 264/134 |
| 5,814,390 A | | 9/1998 | Stokes et al. | 428/181 |
| 5,932,316 A | | 8/1999 | Cree et al. | 428/182 |
| 5,951,798 A | * | 9/1999 | Schmidt et al. | 156/148 |
| 6,588,080 B1 | * | 7/2003 | Neely et al. | 28/122 |
| 6,635,136 B2 | * | 10/2003 | White et al. | 156/204 |
| 2003/0114813 A1 | * | 6/2003 | Dodge et al. | 604/368 |

\* cited by examiner

FIG. 5 — Rush Transfer (on-line) 3.0 osy

MATERIALS HAVING Z-DIRECTION FIBERS AND FOLDS AND METHOD FOR PRODUCING SAME This application claims the benefit of Provisional Application No. 60/132,028, filed Apr. 30, 1999.

BACKGROUND OF THE INVENTION

1. Field of the Invention

This invention relates to a method for producing materials, including films and nonwovens, having z-direction folds or ridges on at least one surface of the material. This invention further relates to a lofty, nonwoven material produced from continuous fibers in which the lofty character of the nonwoven material is the result of the fibers comprising the web having a z-direction orientation, whereby a plurality of ridges or folds are formed on at least one surface of the nonwoven web. These materials are particularly suitable for use in a broad range of applications including fluid management (surge), air and liquid filtration, acoustic and thermal insulation, packing material, absorbents, and cleaning materials. More particularly, these materials are suitable for use as surge, spacer layers, filtration materials and absorbent layers in personal care absorbent products including disposable diapers, incontinence garments, and feminine care products such as sanitary pads and napkins, and in face masks, surgical gowns, sterile wraps and surgical drapes.

2. Discussion of the Related Art

Absorbent personal care articles such as sanitary pads and napkins, disposable diapers, incontinent-care pads and the like are widely used, and much effort has been made to improve their effectiveness and functionality. These articles generally include a liquid absorbent material backed by a liquid-impervious barrier sheet. To enhance the sense of comfort, the absorbent material has a facing of a material which masks at least the body-facing surface of the product. The purpose of this cover material is to help structurally contain the absorbent material and to protect the wearer from continuous direct contact with moisture from previously wetted absorbent material. The cover material is typically of relatively low basis weight nonwoven fabric. Improved product performance has been obtained in these products through the incorporation of a surge management material disposed between the cover material and the absorbent material. The surge management material is made from a relatively high basis weight, low density, that is, thick, nonwoven web material.

In nonwoven webs, the fibers comprising the web are generally oriented in the x-y plane of the web and the resulting nonwoven web material is relatively thin, that is lacking in loft or significant thickness. Loft or thickness in a nonwoven web suitable for use in personal care absorbent articles promotes comfort (softness) to the user, surge management and fluid distribution to adjacent layers.

In order to impart loft or thickness to a nonwoven web, it is generally desirable that at least a portion of the fibers comprising the web be oriented in the z-direction. Conventionally, such lofty nonwoven webs are produced using staple fibers. See, for example, U.S. Pat. No. 4,837,067 which teaches a nonwoven thermal insulating batt comprising structural staple fibers and bonding staple fibers which are entangled and substantially parallel to the faces of the batt at the face portions and substantially perpendicular to the faces of the batt, and U.S. Pat. No. 4,590,114 which teaches a batt including a major percent of thermo- mechanical wood pulp fibers stabilized by the inclusion of a minor percent of thermoplastic fibers including staple length thermoplastic fibers. Alternatively, conventional high loft forming processes rely on pre-forming processes such as fiber crimp formed on a flat wire or drum, and post-forming processes such as creping or pleating of the formed web.

SUMMARY OF THE INVENTION

In contradistinction to the known art the present invention does not first form a web of material and pleat it. Rather, fibers are looped on themselves without being first being formed into a material web. These fiber level loops, running from a first major surface of the web to a second major surface, are aggregated in the cross machine direction to form ridged structures herein sometimes called "waves" or "folds" to distinguish them from "pleats" which refer to structures in preformed web or mesh material that has been folded on itself. A "wavelength" may generally be considered the transit of a loop between its successive trough points on one major surface of the web.

Accordingly, it is one object of this invention to provide a lofty nonwoven web material comprising substantially continuous fibers as opposed to staple fibers traditionally used in the manufacture of such nonwoven materials.

It is yet another object of this invention to provide a method for producing nonwoven materials having z-direction orientation portions.

These and other objects of this invention are addressed by a method for producing a material having z-direction folds comprising conveying a substantially unformed and flat base material of substantially continuous fibers, and added materials if desired, on a first moving surface into a nip formed by the first moving surface and a second moving surface, the second moving surface traveling at a slower speed than the first moving surface, resulting in formation of a plurality of z-direction folds on at least one surface of the material. The method of this invention conveys a material by means of a moving surface into a confined space (the nip) and removes it from the confined space by means of a second moving surface, whereby the rate of removal of the material from the confined space is slower than the rate of material input to the confined surface, resulting in formation of a nonwoven material having z-direction components. The z-direction components produce ridges or ripples on both the major, or x-y surfaces of the material. According to this method the extent of the ridges, and thus the character of the resulting material formed, may be easily affected by a number of operating parameters including, but not limited to, the type of material being processed, geometry of the confined space, the means for transferring the material in the confined space from the first moving surface to the second moving surface, presence or lack of a binding agent such as an adhesive, and the relative speeds of the first and second moving surfaces.

Typically, the size of the confined space (nip) and the relative speeds of the moving surfaces are related with respect to the formation of a web having a desired density of folds. For example, for very low differential speeds between the two moving surfaces, the size of the nip will be very small. As the differential speeds increase, the size of the nip will also increase.

According to certain embodiments herein, a material of this invention, as produced with the method of this invention, comprises a nonwoven web with a plurality of substantially continuous fibers having a z-direction orientation and forming a plurality of ridges on the major surfaces of the nonwoven web.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

As used herein, the term "nonwoven web" or "nonwoven material" means a web having a structure of individual fibers, filaments or threads which are interlaid, but not in a regular or identifiable manner such as those in a knitted fabric or films that have been fibrillated. Nonwoven webs or materials have been formed from many processes such as, for example, meltblowing processes, spunbonding processes, and bonded carded web processes. The basis weight of nonwoven webs or materials is usually expressed in ounces of material per square yard (osy) or grams per square meter (gsm), and the fiber diameters usable are usually expressed in microns. (Note that to convert from osy to gsm, multiply osy by 33.91.)

Figure 3A:
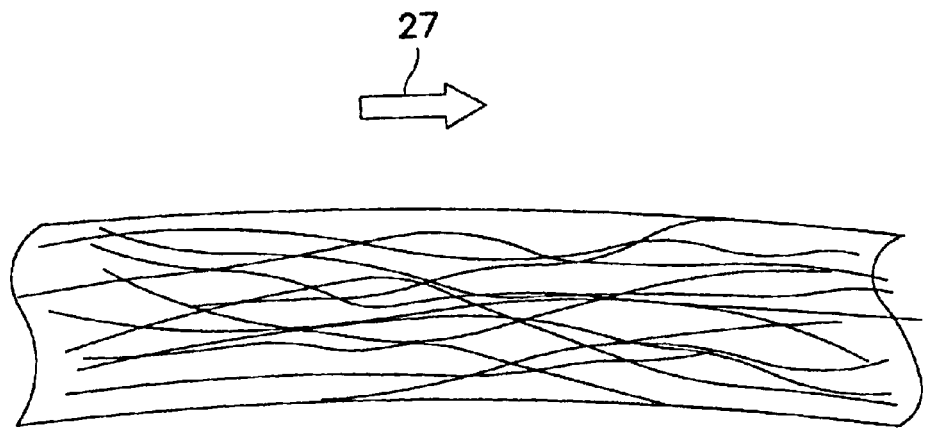
FIGS. 3A and 3B are diagrammatic representations of a conventional nonwoven web and a high loft nonwoven web in accordance with this invention, respectively.
Figure 3B:
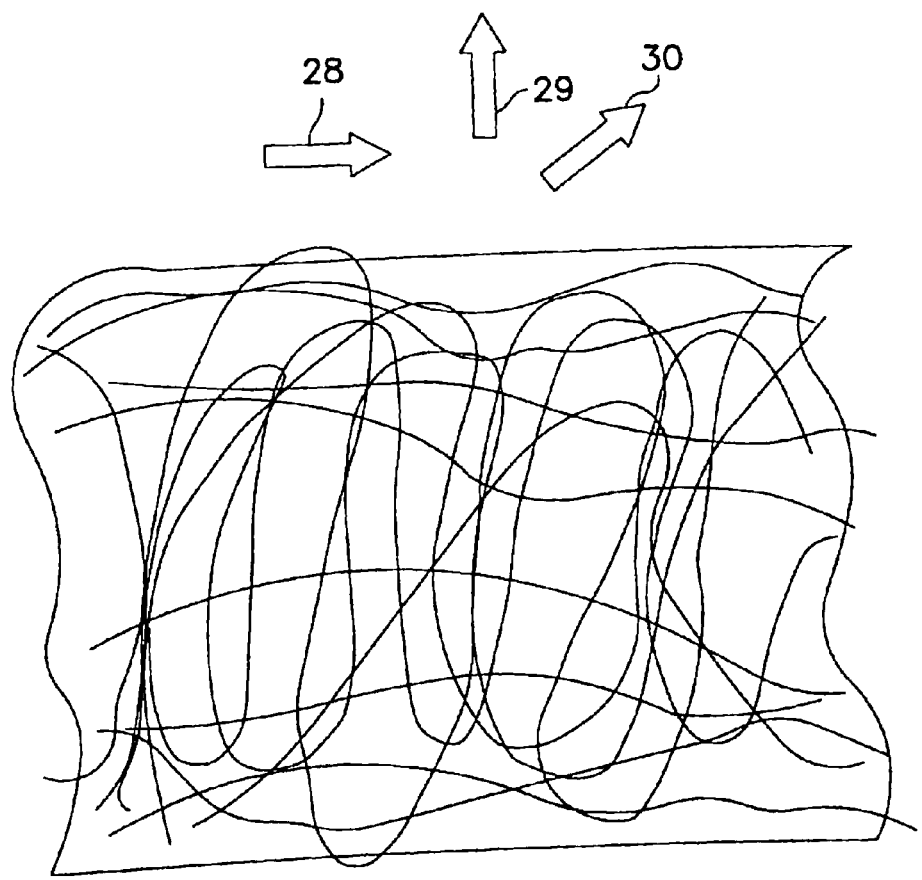

As used herein, the term "z-direction" refers to fibers disposed outside of the plane of orientation of a web. FIG. 3A is a diagram showing a nonwoven web without z-direction fibers. That is, all of the fibers are generally oriented in the direction indicated by arrow 27. By comparison, FIG. 3B is a diagram showing a nonwoven web having z-direction fibers in accordance with this invention. That is, in addition to fibers oriented in the direction of arrow 28, fibers are also oriented in the direction of arrows 29 and 30. The term "as formed z-direction fibers" as used herein refers to fibers that become oriented in the z-direction during forming of the nonwoven web as distinguished from fibers having a z-direction component resulting from post-forming processing of the nonwoven web, such as in the case of mechanically crimped or creped nonwoven webs.

As used herein, the term "spunbond fibers" refers to small diameter fibers which are formed by extruding molten thermoplastic material as filaments from a plurality of fine, usually circular capillaries of a spinneret as taught, for example, by U.S. Pat. No. 4,340,563 to Appel et al. and U.S. Pat. No. 3,802,817 to Matsuki et al.

As used herein, the term "meltblown fibers" refers to fibers formed by extruding a molten thermoplastic material through a plurality of fine, usually circular, die capillaries as molten threads or filaments into converging high velocity gas streams (for example, airstreams) which attenuate the filaments of molten thermoplastic material to reduce their diameter, which may be to microfiber diameter. Such a process is disclosed, for example, by U.S. Pat. No. 3,849,241 to Butin.

As used herein, the term "microfibers" refers to small diameter fibers having an average diameter not greater than about 75 microns, for example, having an average diameter of from about 0.5 microns to about 50 microns, or more particularly, having an average diameter of from about 2 microns to about 40 microns.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" also includes all possible geometric configurations of the material. These configurations include, but are not limited to, isotactic, syndiotactic, atactic and random symmetries.

As used herein, the term "personal care absorbent article" means disposable diapers, training pants, absorbent underpants, adult incontinence products, feminine hygiene products and the like.

As used herein, the term "homofilament" refers to a fiber formed from only one polymer. This is not meant to exclude fibers formed from one polymer to which small amounts of additives have been added for coloration, anti-static properties, lubrication, hydrophilicity, etc.

As used herein, the term "bicomponent fibers" refers to fibers which have been formed from at least two polymers extruded from separate extruders but spun together to form one fiber. Bicomponent fibers are also sometimes referred to as conjugate fibers or multicomponent fibers. Bicomponent fibers are taught by U.S. Pat. No. 5,382,400 to Pike et al.

As used herein, the term "biconstituent fibers" refers to fibers which have been formed from at least two polymers extruded from the same extruder as a blend. The term "blend" is defined below. Biconstituent fibers are sometimes also referred to as multiconstituent fibers. Fibers of this general type are discussed in, for example, U.S. Pat. No. 5,108,827 to Gessner. As used herein, the term "blend" means a mixture of two or more polymers.

As used herein, the term "substantially continuous fibers" refers to fibers, including without limitation, spunbond and meltblown fibers, which are not cut from their original length prior to being formed into a nonwoven web or fabric. Substantially continuous fibers may have average lengths ranging from greater than about 15 centimeters to more than one meter, and up to the length of the web or fabric being formed. The definition of "substantially continuous fibers" includes fibers which are not cut prior to being formed into a nonwoven web or fabric, but which are later cut when the nonwoven web or fabric is cut, and fibers which are substantially linear or crimped.

The term "staple fibers" means fibers which are natural or cut from a manufactured filament prior to forming into a web, and which have an average length ranging from about 0.1–15 centimeters, more commonly about 0.2–7 centimeters.

As used herein, the term "through-air bonding" or "TAB" means the process of bonding a nonwoven, for example, a bicomponent fiber web in which air which is sufficiently hot to melt one of the polymers of which the fibers of the web are made is forced through the web.

As used herein, the term "coform" means a process in which at least one meltblown diehead is arranged near a chute through which other materials are added to the base material or the web while it is forming. Such other materials may be pulp, superabsorbent particles, cellulose or staple fibers, for example. Coform processes are shown in commonly assigned U.S. Pat. No. 4,818,464 to Lau.

Figure 1:
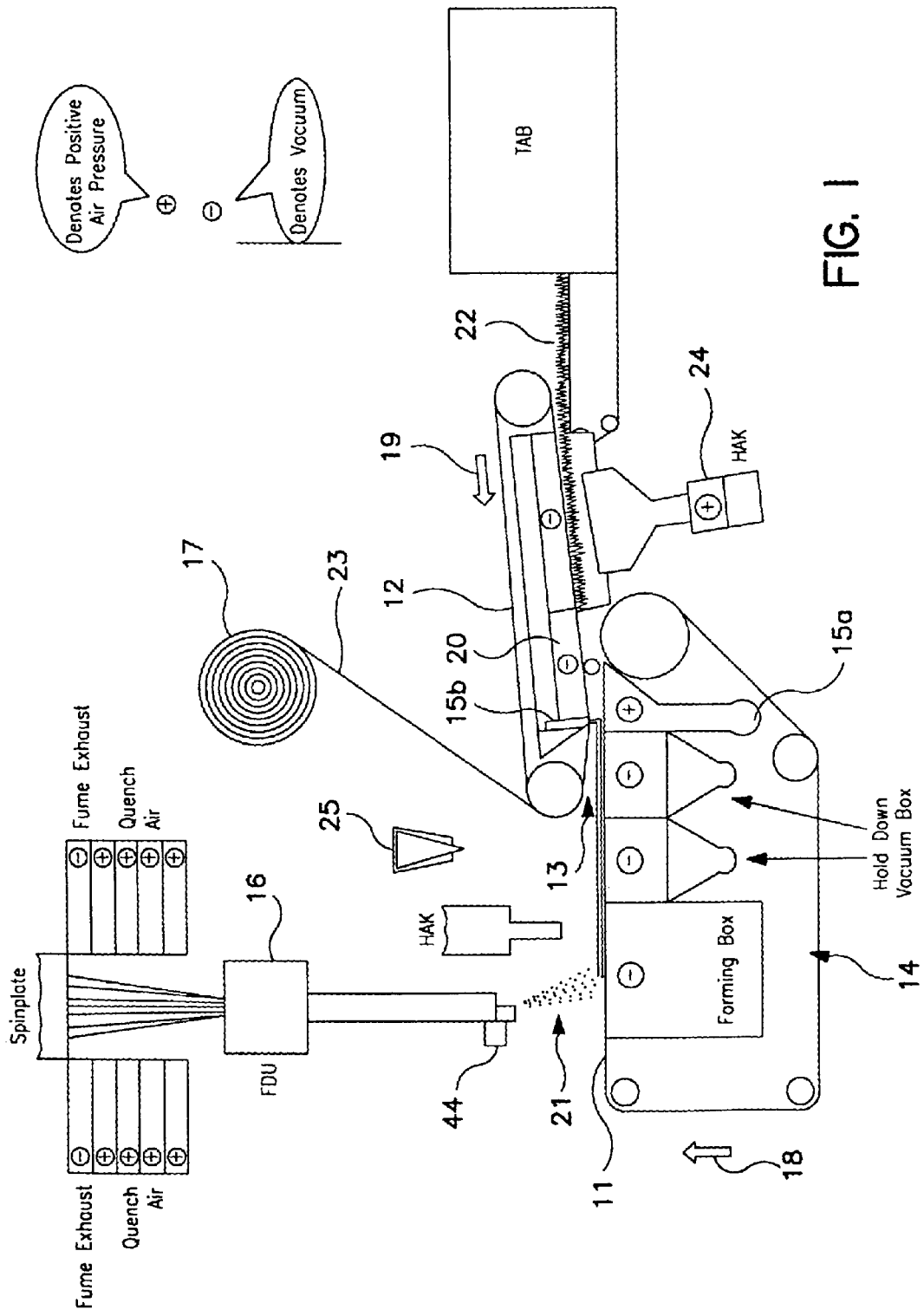
FIG. 1 is a schematic diagram of the method of this invention for producing materials having z-direction components.

FIG. 1 is a schematic diagram showing the method of this invention for producing materials including, but not limited to, films, nonwoven materials and woven materials having z-direction components in the form of ridges or peaks on at least one face. The ridges or peaks formed in accordance with the method of this invention may be regularly spaced or irregular in spacing and shape.

As shown in FIG. 1, a base material 21 of lightly, or nonfunctionally, bonded fibers is transported or conveyed on a first moving surface 11 into the confined space defined by nip 13 formed by first moving surface 11 and second moving surface 12. "Nonfunctionally bonded" is a bonding sufficient only to hold the fibers in place for processing according to the method herein but so light as to not hold the fibers together were there to be manipulated manually. Such bonding may be incidental or eliminated altogether if desirable. A coform unit 44 for adding additional materials to the base material is attached near the outlet of the fiber distribution unit 16. First moving surface 11 is moving in the direction of arrow 18 at a given speed. Base material 21 is held down on first moving surface 11 by a hold down vacuum 14. In nip 13, base material is transferred to second moving surface 12 moving in the direction indicated by arrow 19 via positive air pressure from a blow up box 15a underneath first moving surface 11 and a transfer vacuum 20 beneath the second moving surface. The transfer of the material in nip 13 from first moving surface 11 to second moving surface 12 is accomplished by the application of a transfer vacuum beneath second moving surface 12 generated by high vacuum slot 15b and a transfer vacuum represented by reference numeral 20. It will be appreciated that the present invention may work without a true nip, that is, the first and second surfaces may be serially offset to such a degree that there is no true overlap in their opposite facing surfaces. Second moving surface is moving at a speed slower than the speed of first moving surface 11. First and second moving surfaces are normally foraminous or perforate, wire mesh belts, known in the art as "wires". In accordance with one preferred embodiment of this invention, the speed of first moving surface 11 is in the range of about 1.25 to about 7 times faster than the speed of second moving surface 12.

The confining nature of nip 13 is such that, as the base material 21 of fibers enters nip 13 and is taken away at a slower speed by second moving surface 12, base material 21 accumulates in nip 13 causing the fibers to bunch up and translate into a z-direction displacement until the volume of nip 13 is filled. More specifically, base material 21 moving in the direction indicated by arrow 18 encounters a slowdown in nip 13 as a result of which the base material 21 moves in the z-direction until it hits the surface of second moving surface 12 and is removed thereby. As a result, the material exiting from nip 13 comprises at least one surface, and normally both surfaces, having ridges or peaks as indicated by reference numeral 22.

Although suitable for producing ridged films and pleated wovens, the method of this invention is particularly suitable for producing preponderantly open, or low density, nonwoven webs of continuous fibers having z-direction components. Specifically, the material produced in accordance with a preferred embodiment of this invention is a nonwoven web comprising a plurality of substantially continuous fibers having a z-direction orientation and forming the ridges or peaks 22.

The substantially continuous fibers are preferably selected from the group consisting of homofilament fibers, bicomponent fibers, biconstituent fibers and combinations thereof. The substantially continuous fibers are preferably formed with polymers selected from the group consisting of polyolefins, polyamides, polyesters, polycarbonates, polystyrenes, thermoplastic elastomers, fluoropolymers, vinyl polymers, and blends and copolymers thereof.

Suitable polyolefins include, but are not limited to, polyethylene, polypropylene, polybutylene, and the like; suitable polyamides include, but are not limited to, nylon 6, nylon 6/6, nylon 10, nylon 12 and the like; and suitable polyesters include, but are not limited to, polyethylene terephthalate, polybutylene terephthalate and the like. Particularly suitable polymers for use in the present invention are polyolefins including polyethylene, for example, linear low density polyethylene, low density polyethylene, medium density polyethylene, high density polyethylene and blends thereof; polypropylene; polybutylene and copolymers as well as blends thereof. Additionally, the suitable fiber forming polymers may have thermoplastic elastomers blended therein. In addition, staple fibers may be employed in the nonwoven web as a binder.

In order to provide stability to the product material, the nonwoven web is bonded, either by application of an adhesive from adhesive system 25 or by thermal bonding such as by through-air bonding, a calender, or the like, or by means of a hot air knife (HAK) 24. A hot air knife is used to bond the individual polymer fibers together at various locations so that the web has increased strength and structural integrity for subsequent treatments such as passage through a through-air bonding (TAB) unit. A conventional hot air knife includes a mandrel with a slot that blows a jet of hot air onto the nonwoven web surface. Such hot air knives are taught, for example, by U.S. Pat. No. 5,707,468 to Arnold et al.

As shown in FIG. 1, a base material 21 of substantially continuous fibers is fed onto first moving surface 11 from a Fiber Distribution Unit 16 as at reference numeral 16. However, it will be apparent to those skilled in the art that certain base material 21 fibers may be formed directly on first moving surface 11 or unwound from prewound spools or the like.

Base materials suitable for use in the material and method of this invention are preferably selected from the group consisting of spunbond, meltblown, spunbond-meltblown-spunbond laminates, coform, spunbond-film-spunbond laminates, bicomponent spunbond, bicomponent meltblown, biconstituent spunbond, biconstituent meltblown, pulp, superabsorbent, and combinations thereof.

The characteristics of the material produced in accordance with the method of this invention may be varied by varying such method elements as nip geometry, including the vertical distance between first moving surface 11 and second moving surface 12 as well as the extent of overlap between first moving surface 11 and second moving surface 12, vacuum strength and location, bonding mechanism, and speeds of the material entering and leaving nip 13. The type of fiber will of course have an affect on the morphology of the web made. In addition, although the present invention generally produces a self-supporting lofty web, the end product may include a support structure or a second material 23, as shown being introduced into nip 13 from the unwind designated by reference numeral 17.

Figure 2:
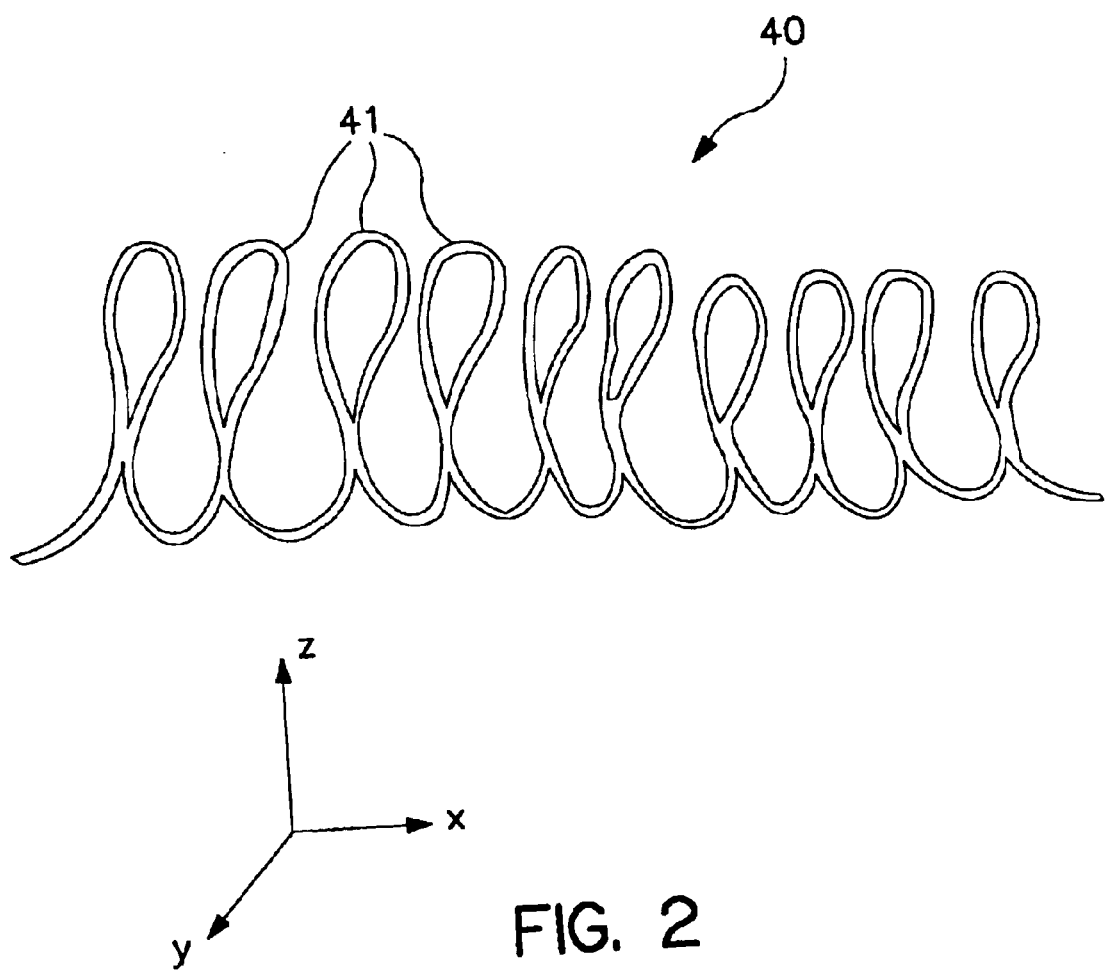
FIG. 2 is a diagram of a side view of a nonwoven web having z-direction components in the form of ridges or ripples formed in accordance with the method of this invention.

FIG. 2 is a diagram showing a side view of a z-direction component nonwoven web 40 produced in accordance with the method of this invention comprising ridges 41 formed by substantially continuous fibers.

Figure 4:
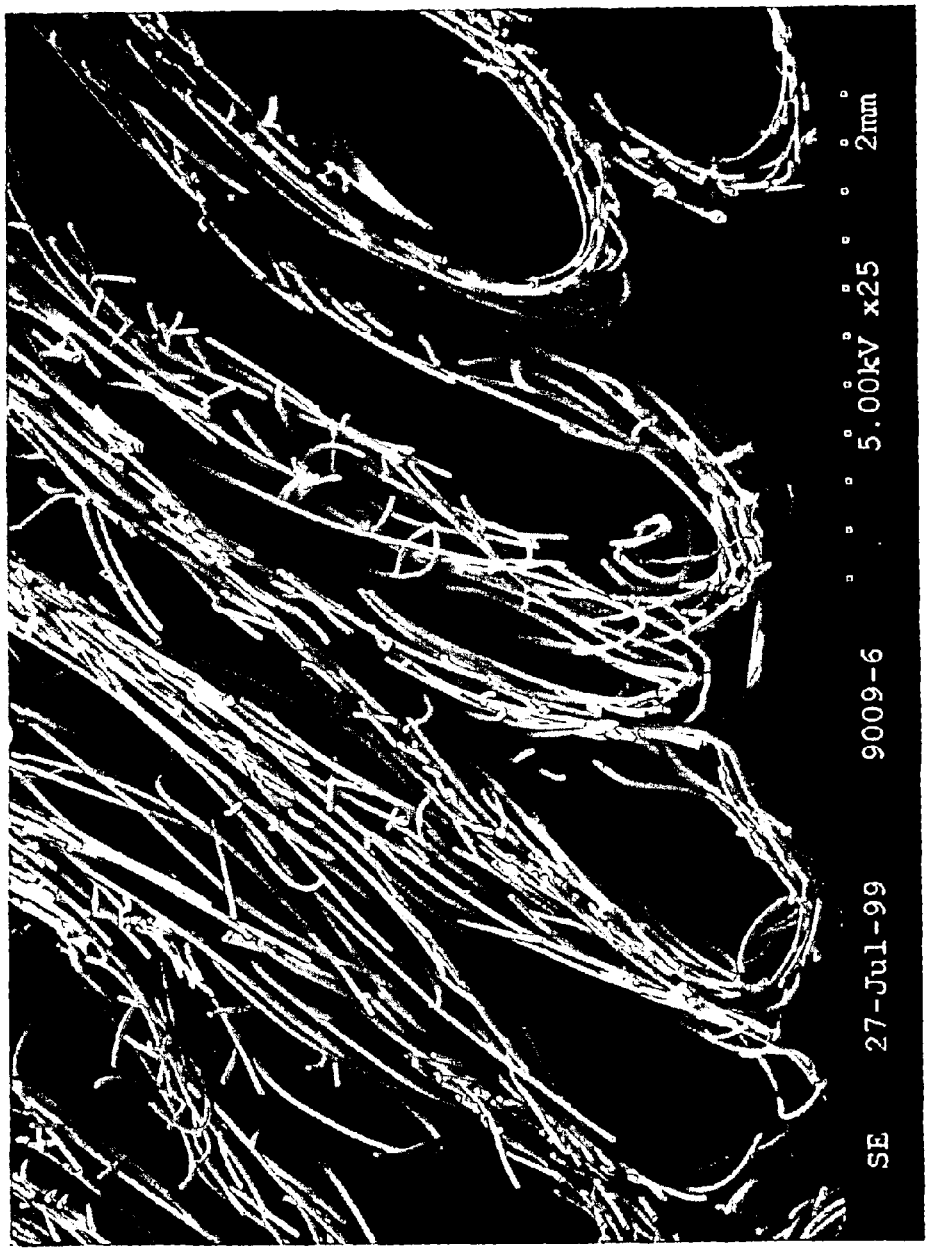
FIGS. 4–9 are photographs in side view of nonwoven materials produced in accordance with the method of this invention showing various loop structures.

FIG. 4 is a photograph of a side view of a nonwoven web produced in accordance with the method of this invention for a 2.5 osy basis weight in which the sheath/core bicomponent straight individual fibers are readily visible showing regularly and elliptically shaped looped fibers at both major surfaces of the web. The web is substantially open and forms a plurality of channels running in the cross machine direction between loops. The loops are oriented off the true z-axis and are unidirectional, i.e. all leaning one way. A nonwoven web according to the present invention has a basis weight preferably in the range of about 0.25 osy to about 50 osy.

Figure 5:

FIG. 5 is a photograph of a side view of a nonwoven web produced in accordance with the method of this invention, but at a higher speed differential than FIG. 4, for a 3.0 osy basis weight and in which the substantially continuous individual fibers are readily visible showing slightly more random but still basically elliptically shaped looped fibers at both major surfaces of the web. The web is substantially open, i.e. the fibers are not tightly packed and the web exhibits a preponderance of air spaces rather than fiber at its surfaces, and the web forms a plurality of channels is running in the cross machine direction between loops. In terms of gross morphology the material of FIG. 5 will have smoother surfaces and less evident ridges than that of FIG. 4.

Figure 6:

FIG. 6 is a photograph of a side view of a nonwoven web produced in accordance with the method of this invention, but with crimped rather than straight fibers, for a 3.2 osy basis weight and in which the substantially continuous individual fibers are readily visible showing even more random, but still basically elliptically shaped looped fibers at both major surfaces of the web. The web is substantially open but does not show distinct channels running in the cross machine direction between loops. In terms of gross morphology the material of FIG. 6 will have broader and less regular ridges, i.e. "regular" referring to the periodicity of pleats in the machine direction and the frequency with which the pleats extend from edge to edge in the cross direction than that of FIG. 5.

Figure 7:

FIG. 7 is a photograph of a side view of a nonwoven web produced in accordance with the method of this invention, but at a still higher speed differential, for a 4.0 osy basis weight and in which the looped fibers are highly compressed. The tightly elliptical looped fibers do not show channels between the waves. The web is becoming more closed than open in nature. In terms of gross morphology the material of FIG. 7 will have still smoother surfaces and less evident ridges than those of the previous figures.

Figure 8:
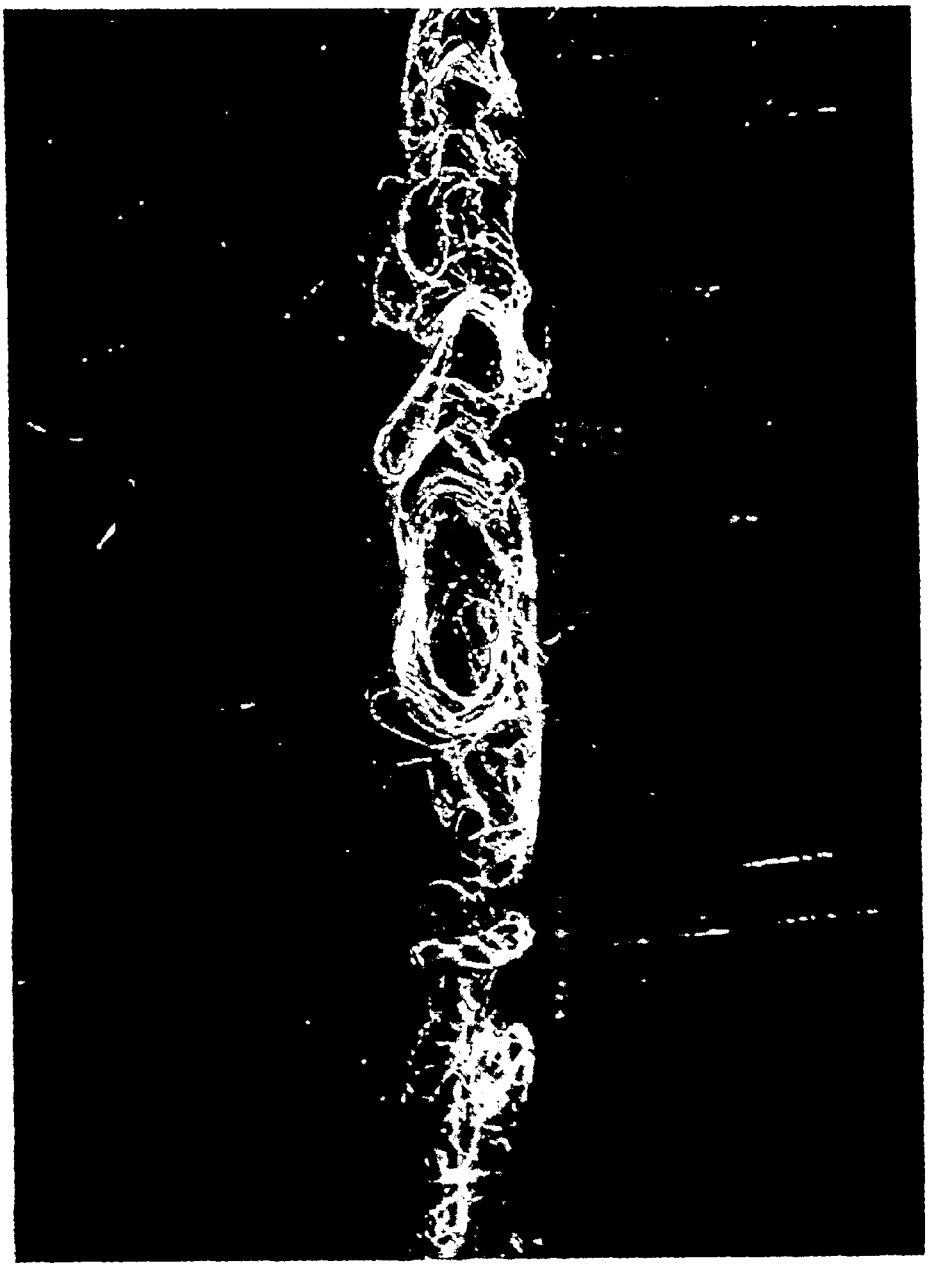

FIG. 8 is a photograph of a side view of a nonwoven web produced in accordance with the method of this invention, but at a low 0.5 osy basis weight and in which the substantially continuous individual fibers are readily visible showing quite random waving to the point of losing the basically elliptically shaped and regular periodicity waving on the surface of the web. The loops may be considered multidirectional, i.e. leaning at random away from the orthogonal z-axis. The web is very open. In terms of gross morphology the material of FIG. 8 will have smooth surfaces, less evident ridges and many thin spots.

Figure 9:

FIG. 9 is a photograph of a side view of a nonwoven web produced in accordance with the method of this invention, but with side by side bicomponent crimped fibers at a low 0.8 osy basis weight again showing quite random waving. As would be expected, the web shows a lack of regular periodicity waving on the surface. The web is very open. In terms of gross morphology the material of FIG. 9 will have smooth surfaces, almost nonevident ridges and many thin spots.

In accordance with one preferred embodiment of this invention, the substantially continuous fibers are bicomponent fibers. Particularly suitable polymers for forming the structural component of suitable bicomponent fibers include polypropylene and copolymers of polypropylene and ethylene, and particularly suitable polymers for the adhesive component of the bicomponent fibers includes polyethylene, more particularly linear low density polyethylene, and high density polyethylene. In addition, the adhesive component may contain additives for enhancing the crimpability and/or lowering the bonding temperature of the fibers, and enhancing the abrasion resistance, strength and softness of the resulting webs.

The nonwoven web of the material of this invention has a basis weight in the range of about 0.25 osy to about 50 osy. To enhance the absorption characteristics of the nonwoven material, in accordance with one embodiment of this invention, the nonwoven web comprises an absorbent, for example, superabsorbent particles. In accordance with one embodiment of this invention, a support structure is attached to at least one face of the nonwoven web so as to provide strength thereto. The resulting laminate structure provides support for the high loft structure, strength for winding, converting, etc., and a boundary layer to either enhance or retard fluid flow into the lofty absorbent structure. The support structure may include spunbond webs of various types including liners, perforated, micro-fiber, creped, etc., spunbond-meltblown-spunbond (SMS), meltblown, and/or films.

Potential applications for the nonwoven web of this invention include personal care absorbent articles such as diapers, training pants, incontinence garments, feminine care products including sanitary pads and napkins, all surge materials, loop for hook and loop, air filtration, liquid filtration, body scrub pads, oil sorb, industrial and baby wipes, insulation material, packaging material, and translucent or shading material for lamp shades or the like. In the case of filtration materials, the method of this invention greatly increases the surface area available for filtration. In addition, the method of this invention may be suitable for pleating fabrics. And, for rolls of diapers, a composite material could be produced by ridging or ruffling a high loft surge/pulp/superabsorbent material laminate and placing it in between an outer cover and a liner, which would produce a laminate with all of the components of a diaper in a single step, which could be wound up and cut and placed later on converting machines.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A material comprising:
   a nonwoven web comprising a plurality of substantially continuous as formed z-direction fibers having a z-direction orientation and forming a plurality of closed loops of fibers between both x-y plane surfaces of the nonwoven web, the closed loops defining open spaces within the web and being formed without pleating of the web.

2. A lofty material comprising:
   a nonwoven web comprising a plurality of substantially continuous as formed z-direction fibers,
   the web being a lofted web with x, y and z dimensions, with x being the machine direction, y being the cross machine direction and z being the loft direction;

the web having first and second major surfaces in x-y planes and spaced apart in the z direction;

the continuous fibers being folded to form closed loops of fibers extending in the z direction, the closed loops defining open spaces within the web, and the closed loops combining to form a material with a succession of channels spaced along the machine direction, each channel running in the cross machine direction and being formed without pleating of the web.

3. The material according to claim 2 further including each closed loop having at least one of a leading or trailing edge bonded to an adjacent closed loop leading or trailing edge to thereby hold its z-direction shape.

4. The material according to claim 3 wherein the leading and trailing edges of one closed loop are bonded together.

5. The material according to claim 3 wherein the leading and trailing edges of one closed loop are bonded together and bonded to the trailing and leading edges of the adjacent closed loops, respectively.

6. The material according to claim 2 further including each closed loop being substantially elliptically shaped in cross section between the major surfaces.

7. The material according to claim 2 further including: the closed loops being oriented off the orthogonal z-axis and being unidirectional.

8. The material according to claim 2 further including: the closed loops being oriented off the orthogonal z-axis and being multi-directional.

9. The material according to claim 2 further including: the first major surface being preponderantly closed.

10. The material according to claim 2 further including: the second major surface being preponderantly closed.

11. The material according to claim 2 further including: the channels being randomly spaced in the machine direction.

12. The material according to claim 2 further including: the channels being regularly spaced in the machine direction.

13. The material according to claim 2 further including: the channels being of random length in the cross machine direction.

14. The material according to claim 2 further including: the channels being of regular length in the cross machine direction.

15. A personal care absorbent article comprising: a nonwoven web comprising a plurality of substantially continuous as formed z-direction fibers having a z-direction orientation and forming a plurality of closed loops of fibers between both x-y plane surfaces of the nonwoven web, the closed loops defining open spaces within the web and being formed without pleating of the web.

16. A personal care absorbent article in accordance with claim 15, wherein the nonwoven web further comprises an absorbent.

17. A filtration material comprising: a nonwoven web comprising a plurality of substantially continuous as formed z-direction fibers having a z-direction orientation and forming a plurality of closed loops of fibers at at least one surface of the nonwoven web, the closed loops defining open spaces within the web and being formed without pleating of the web.

18. A filtration material in accordance with claim 17, wherein a support structure is attached to at least one face of the nonwoven web.

19. A material comprising:
a nonwoven web comprising a plurality of substantially continuous as formed z-direction fibers having a z-direction orientation and forming a plurality of closed loops of fibers between both x-y plane surfaces of the nonwoven web, the loops combining in the cross direction to form a channel within the web running in the cross machine direction of the material and being formed without pleating of the web.

20. A lofty material comprising:
a nonwoven web comprising a plurality of substantially continuous as formed z-direction fibers, the web being a lofted web with x, y and z dimensions, with x being the machine direction, y being the cross machine direction and z being the loft direction;

the web having first and second major surfaces in x-y planes and spaced apart in the z direction;

the continuous fibers being folded to form loops of fibers extending in the z direction, the loops defining open spaces within the web, and the loops combining in the cross direction to form a succession of channels spaced along the machine direction, each channel running in the cross machine direction of the material and being formed without pleating of the web.

21. A personal care absorbent article comprising:
a nonwoven web comprising a plurality of substantially continuous as formed z-direction fibers having a z-direction orientation and forming a plurality of loops of fibers between both x-y plane surfaces of the nonwoven web, the loops aggregating in the cross direction to define a series of open channels within the web extending in the cross direction of the web and being formed without pleating of the web.

22. A filtration material comprising: a nonwoven web comprising a plurality of substantially continuous as formed z-direction fibers having a z-direction orientation and forming a plurality of loops of fibers at at least one surface of the nonwoven web, the closed loops aggregating in the cross direction to define open spaces within the web extending in the cross direction of the web and being formed without pleating of the web.

* * * * *